(12) United States Patent
Elrod

(10) Patent No.: US 10,752,501 B2
(45) Date of Patent: *Aug. 25, 2020

(54) SCENT ELIMINATION DEVICE FOR HUNTERS IN THE FIELD

(71) Applicant: PARAH, LLC, Lake Jackson, TX (US)

(72) Inventor: Scott A. Elrod, Lake Jackson, TX (US)

(73) Assignee: PARAH, LLC, Lake Jackson, TX (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/184,669

(22) Filed: Nov. 8, 2018

(65) Prior Publication Data

US 2019/0112190 A1    Apr. 18, 2019

Related U.S. Application Data

(63) Continuation of application No. 14/052,448, filed on Oct. 11, 2013, now abandoned, which is a continuation of application No. 13/099,270, filed on May 2, 2011, now Pat. No. 8,557,177, which is a continuation of application No. 11/018,620, filed on Dec. 21, 2004, now Pat. No. 7,939,015.

(51) Int. Cl.
| | |
|---|---|
| *C01B 13/11* | (2006.01) |
| *A61L 2/18* | (2006.01) |
| *A61L 9/015* | (2006.01) |
| *A61L 9/20* | (2006.01) |

(52) U.S. Cl.
CPC ............ *C01B 13/11* (2013.01); *A61L 2/183* (2013.01); *A61L 9/015* (2013.01); *A61L 9/20* (2013.01)

(58) Field of Classification Search
CPC . A61L 9/20; A61L 9/015; A61L 2/183; C01B 13/11
See application file for complete search history.

(56) References Cited

U.S. PATENT DOCUMENTS

| | | |
|---|---|---|
| 1,961,878 A | 6/1934 | Gilkey |
| 2,203,188 A | 6/1940 | Beer |
| 3,214,364 A | 10/1965 | Tuyle et al. |
| 3,421,836 A | 1/1969 | Sundin et al. |
| 3,601,292 A | 8/1971 | Bliss |
| 3,670,425 A | 6/1972 | Benjamin |
| 3,750,556 A | 8/1973 | Duke |
| 3,937,967 A | 2/1976 | Steinitz |
| 3,949,056 A | 4/1976 | Nakshbendi |
| 4,045,316 A | 8/1977 | Legan |
| 4,238,857 A | 12/1980 | Waters |
| 4,309,388 A | 1/1982 | Tenney et al. |
| 4,374,571 A | 2/1983 | Hirvela |
| 4,735,010 A | 4/1988 | Grinarml |
| 4,811,159 A | 3/1989 | Foster |
| 4,863,687 A | 9/1989 | Stevens et al. |
| 4,867,052 A | 9/1989 | Cipelletti |
| 4,904,289 A | 2/1990 | Miyakami et al. |
| 4,941,270 A | 7/1990 | Hoffman |
| 4,953,674 A | 9/1990 | Landes |
| 4,990,311 A | 2/1991 | Hirai et al. |
| 5,087,426 A | 2/1992 | Inoue et al. |
| 5,152,077 A | 10/1992 | Liang |
| 5,185,129 A | 2/1993 | Koutrakis et al. |
| 5,192,500 A | 3/1993 | Treddenick |
| 5,303,496 A | 4/1994 | Kowalkowski |
| 5,316,182 A | 5/1994 | Lee et al. |
| 5,342,415 A | 8/1994 | Wasinger et al. |
| 5,383,236 A | 1/1995 | Sesselmann |
| 5,429,271 A | 7/1995 | Porter |
| 5,433,230 A | 7/1995 | Miller |
| 5,433,919 A | 7/1995 | Baltes |
| 5,450,977 A | 9/1995 | Moe |
| 5,457,054 A | 10/1995 | Geisinger et al. |
| 5,468,454 A | 11/1995 | Kim |
| 5,484,472 A | 1/1996 | Weinberg |
| 5,514,345 A | 5/1996 | Garbutt et al. |
| 5,520,893 A | 5/1996 | Kasting et al. |
| 5,539,930 A | 7/1996 | Sesselmann |
| 5,547,476 A | 8/1996 | Siklosi et al. |
| 5,667,564 A | 9/1997 | Weinberg |
| 5,681,355 A | 10/1997 | Davis et al. |
| 5,762,648 A | 6/1998 | Yeazell |
| 5,766,560 A | 6/1998 | Cole |
| 5,788,930 A | 8/1998 | McMurray |

(Continued)

FOREIGN PATENT DOCUMENTS

| | | |
|---|---|---|
| EP | 0261987 A2 | 3/1988 |
| JP | H02165049 A | 6/1990 |

(Continued)

OTHER PUBLICATIONS

Bomms Terminator. Game Finder—Outdoor Enhancement Systems, Web page print outs from http://www.game-finder.com/bomms-terminator.aspx, printed on Dec. 23, 2006 (2 pages).
Certified English Translation of JP3423164.
"BOMMS Terminator", Game Finder, May 24, 2002.
"Terminator 800", Game Finder, Feb. 13, 2003.
McElhiney et al., "Detection of the Cyanobacterial Hepatoxins Microsystins", Toxicology & Applied Pharmacology, Dec. 1, 2003, pp. 219-230.
Fehrenbacher, J. , "Robotic Pollution-Sniffing Eco Dogs!", [online], retrieved from the internet: URL: http://inhabitat.com/robotic-pollution-sniffing-eco-dogs/, Feb. 26, 2007.

(Continued)

*Primary Examiner* — Regina M Yoo

(74) *Attorney, Agent, or Firm* — Dorsey & Whitney LLP

(57) ABSTRACT

A scent elimination device 100 for removing the human scent and any other scent associated with hunters in the field. The device 100 produces ozone, which is applied directly or indirectly to the clothing, equipment and body 300 while the hunter is in the field 200 and/or prior to or after the hunt. The method can also be used by fishermen to eliminate fish odor.

16 Claims, 1 Drawing Sheet

(56) References Cited

U.S. PATENT DOCUMENTS

| | | |
|---|---|---|
| 5,789,368 A | 8/1998 | You et al. |
| 5,790,987 A | 8/1998 | Sesselmann |
| 5,795,544 A | 8/1998 | Matz |
| 5,820,828 A | 10/1998 | Ferone |
| 5,829,066 A | 11/1998 | Aibe |
| 5,833,740 A | 11/1998 | Brais |
| 5,835,840 A | 11/1998 | Goswami |
| 5,891,391 A | 4/1999 | Fore |
| 5,911,957 A | 6/1999 | Khatchatrian et al. |
| 5,931,014 A | 8/1999 | Cole |
| 5,942,438 A | 8/1999 | Antonoplos et al. |
| 5,983,834 A | 11/1999 | Tai |
| 6,007,770 A | 12/1999 | Peiper et al. |
| 6,009,559 A | 1/2000 | Sesselmann |
| 6,032,682 A | 3/2000 | Verhaverbeke |
| 6,074,608 A | 6/2000 | Matz |
| 6,094,549 A | 7/2000 | Hiraoka et al. |
| 6,134,718 A | 10/2000 | Sesselmann |
| 6,134,806 A | 10/2000 | Dhaemers |
| 6,149,038 A | 11/2000 | Tsai |
| 6,153,111 A | 11/2000 | Conrad et al. |
| 6,156,268 A | 12/2000 | Curry et al. |
| 6,163,098 A | 12/2000 | Taylor et al. |
| 6,182,671 B1 | 2/2001 | Taylor et al. |
| 6,218,189 B1 | 4/2001 | Antonoplos et al. |
| 6,267,242 B1 | 7/2001 | Nagata et al. |
| 6,284,204 B1 | 9/2001 | Cole et al. |
| 6,312,507 B1 | 11/2001 | Taylor et al. |
| 6,336,964 B1 | 1/2002 | Omatsu et al. |
| 6,340,447 B2 | 1/2002 | Johnson |
| 6,340,497 B2 | 1/2002 | Wilson |
| 6,355,216 B1 | 3/2002 | Kristiansson et al. |
| 6,368,867 B1 | 4/2002 | Gibson et al. |
| 6,379,435 B1 | 4/2002 | Fukunaga et al. |
| 6,503,547 B1 | 1/2003 | Lima |
| 6,564,591 B2 | 5/2003 | Noyes et al. |
| 6,565,805 B2 | 5/2003 | Khatchatrian et al. |
| 6,576,190 B1 | 6/2003 | Park |
| 6,613,277 B1 | 9/2003 | Monagan |
| 6,630,105 B1 | 10/2003 | O×Neill et al. |
| 6,632,407 B1 | 10/2003 | Lau et al. |
| 6,635,439 B2 | 10/2003 | Morrison et al. |
| 6,679,419 B1 | 1/2004 | Sarracino |
| D486,357 S | 2/2004 | Leba et al. |
| 6,790,411 B1 | 9/2004 | Read |
| 6,896,853 B2 | 5/2005 | Law et al. |
| 6,967,008 B1 | 11/2005 | Barnes |
| 7,117,687 B2 | 10/2006 | Naaman |
| 7,118,608 B2 | 10/2006 | Lovell |
| 7,186,373 B2 | 3/2007 | Centanni |
| 7,222,634 B2 | 5/2007 | Hess et al. |
| 7,662,636 B2 | 2/2010 | Maruo et al. |
| 7,939,015 B1 * | 5/2011 | Elrod .................. A61L 2/183 422/5 |
| 8,066,939 B2 | 11/2011 | Elrod |
| 8,557,177 B1 * | 10/2013 | Elrod .................. A61L 2/183 422/5 |
| 2002/0030022 A1 | 3/2002 | Bradley |
| 2002/0071795 A1 | 6/2002 | Jensen |
| 2002/0094298 A1 | 7/2002 | Monagan |
| 2002/0127137 A1 | 9/2002 | Scepanski |
| 2003/0035764 A1 | 2/2003 | Thomas et al. |
| 2003/0044308 A1 | 3/2003 | Toth |
| 2003/0066767 A1 | 4/2003 | Felsenthal |
| 2003/0089010 A1 | 5/2003 | Wechter et al. |
| 2003/0108460 A1 | 6/2003 | Andreev et al. |
| 2003/0111435 A1 | 6/2003 | Chen |
| 2003/0192562 A1 | 10/2003 | Higashi et al. |
| 2004/0002349 A1 | 1/2004 | Yamagishi et al. |
| 2004/0047775 A1 | 3/2004 | Lau et al. |
| 2004/0047776 A1 | 3/2004 | Thomsen |
| 2004/0096354 A1 | 5/2004 | Nomura et al. |
| 2004/0149329 A1 | 8/2004 | Hess et al. |
| 2004/0163184 A1 | 8/2004 | Waldron et al. |
| 2004/0221396 A1 | 11/2004 | Johnson |
| 2005/0028254 A1 | 2/2005 | Whiting |
| 2005/0123436 A1 | 6/2005 | Cumberland |
| 2005/0186108 A1 | 8/2005 | Fields |
| 2005/0207951 A1 | 9/2005 | Lee et al. |
| 2005/0263387 A1 | 12/2005 | Thomas et al. |
| 2005/0284745 A1 | 12/2005 | Smith |
| 2006/0006122 A1 | 1/2006 | Burns et al. |
| 2006/0096331 A1 | 5/2006 | Kim |
| 2006/0151896 A1 | 7/2006 | Wang |
| 2006/0177412 A1 | 8/2006 | Janardanan et al. |
| 2006/0266221 A1 | 11/2006 | Fink et al. |
| 2007/0092414 A1 | 4/2007 | Malyon |
| 2007/0166186 A1 | 7/2007 | Stec |
| 2007/0212253 A1 | 9/2007 | Elrod |
| 2008/0036594 A1 | 2/2008 | Kates |
| 2008/0159910 A1 | 7/2008 | Dick et al. |
| 2008/0213125 A1 | 9/2008 | Boast et al. |
| 2009/0038555 A1 | 2/2009 | Reese |
| 2009/0139459 A1 | 6/2009 | Habacivch et al. |
| 2010/0071633 A1 | 3/2010 | Elrod |
| 2010/0107991 A1 | 5/2010 | Elrod |
| 2010/0289655 A1 | 11/2010 | Elrod et al. |
| 2014/0178255 A1 | 6/2014 | Elrod |

FOREIGN PATENT DOCUMENTS

| | | | |
|---|---|---|---|
| JP | 02302666 | | 12/1990 |
| JP | 06327749 A | | 11/1994 |
| JP | 08168363 A | | 7/1996 |
| JP | 3423164 B2 | | 10/1996 |
| JP | 409220274 A | | 8/1997 |
| JP | 09239018 A | | 9/1997 |
| JP | 09262141 A | | 10/1997 |
| JP | 11009948 A | | 1/1999 |
| JP | 11009949 A | | 1/1999 |
| JP | 11226106 A | | 8/1999 |
| JP | 11226108 A | | 8/1999 |
| JP | 2002345937 A | | 12/2002 |
| JP | 2003001237 A | | 1/2003 |
| JP | 2003024426 A | | 1/2003 |
| RO | 96711 A2 | | 4/1989 |
| WO | 0151096 A2 | | 7/2001 |
| WO | 0177283 A1 | | 10/2001 |
| WO | 03089017 A1 | | 10/2003 |
| WO | WO-03089017 A1 * | 10/2003 | ............... A61L 2/10 |
| WO | 2004067043 A2 | | 8/2004 |
| WO | 2005021135 A1 | | 3/2005 |
| WO | 2005077425 A1 | | 8/2005 |

* cited by examiner

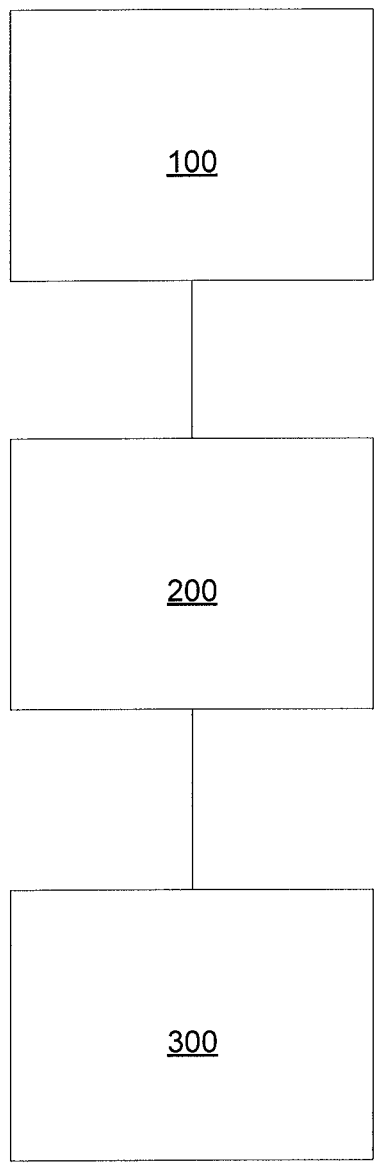

SCENT ELIMINATION DEVICE FOR HUNTERS IN THE FIELD

RELATED APPLICATIONS

This is a continuation of U.S. patent application Ser. No. 14/052,448, filed on 11 Oct. 2013, now abandoned, which is a continuation of U.S. patent application Ser. No. 13/099,270, filed on 2 May 2011, now U.S. Pat. No. 8,557,177, which is a continuation of U.S. patent application Ser. No. 11/018,620, filed on 21 Dec. 2004, now U.S. Pat. No. 7,939,015, the disclosures of which are incorporated, in their entireties, by this reference.

FIELD OF THE INVENTION

The invention relates to a method of de-scenting the clothes and apparatus of sportsmen, both professional, non-professional, bikers, campers and the like. More particularly, there is provided a method of removing human scent and any other scent that is not advantageous in that environment from clothing and equipment of hunters and fish odors from fisherman utilizing an oxidizing agent which is ozone or a combination of hydroxyl and hydroperoxide ions.

BACKGROUND OF THE INVENTION

Animals have an acute sense of smell and are capable of recognizing a human scent or any other scent that is not advantageous in that environment at long distances. To avoid such recognition a hunter will attempt to stay down wind of the animal being hunted. The more common method used by hunters to trick the animals is to mask the human odor utilizing an animal scent. Unfortunately the animal scents which are utilized, are obnoxious and linger on the clothing for long periods of time. Some of the scents utilized include animal urine. A hunter who is camping overnight does not desire the animal scents to be carried over to bedtime, home, car, etc.

There are other drawbacks in utilizing animal scents or any other scents. The scent may attract a predator of the game which the hunter is not hunting for which the hunter may not be prepared to encounter. Descenting packs or containers containing food or any other substance that contains scents that may not be natural to the given environment. Also, the weapon used by the hunter has an odor recognizable by some animals which cannot be disguised with a scent.

Fishermen have the problem of fish odor on their hands and clothes which is difficult to remove. For fishermen camping overnight the fish odor is not only undesirable because of the odor but can also attract animals such as bears which the fishermen is not prepared to meet.

Hunters have prepared their clothing before hand by washing to remove prior scents and/or human odor. The washing materials may also leave an odor. However, out in the field the hunter can sweat and permeate the clothing with a human scent. It would be desirable to deodorize clothing during a hunt or while on a fishing trip.

Ozone has been used for decontaminating buildings and for deodorizing denim garment. U.S. Pat. No. 5,833,740 to Brais discloses an apparatus for sterilizing bottles utilizing ozone. The reference recognizes that ozone in large quantities can be harmful or irritating. Consequently, it was necessary to provide means for decomposing the excess ozone and/or to cause its escape into the atmosphere.

Ozone is a powerful oxidizing agent. Ozone has 150% of the oxidizing potential of chlorine and twice the oxidizing potential of bromine. Ozone has been shown to be much more effective than chlorine with a reaction time up to 10 times faster. Ozone also readily self-destructs into simple diatomic oxygen due to its inherent instability. Ozone oxidizes biological products and kills bacteria.

Catalytic ionization using ultraviolet light is known to produce a mixture of hydroxyl and hydroperoxide ions. Ionization devices which are used in automobiles to eliminate smoke and odors are known in the art to product hydroxyl and hydroperoxide ions.

BRIEF DESCRIPTION OF THE DRAWING

FIG. 1 is a schematic drawing of a scent elimination device, as used in the field.

SUMMARY OF THE INVENTION

The invention relates to a method for deodorizing the clothing apparatus of sportsmen, professional or non-professional. More particularly, there is provided a method for removing human scent or any other foreign scent of clothing used by hunters before or during a hunt through the use of ozone or hydroxyl and hydroperoxide ions produced by ionization in a manner that would not cause irritation or injury to the user or equipment. Also, there is provided a method for removing fish odor from fishermen and their clothing and equipment while in the field, including lures, tackle boxes and containers. The principal objective of the invention is the provision of a method for effectively removing human scent from clothing used by sportsmen.

It is another object of the invention to deodorize fish odor on fishermen.

It is yet another object of the invention to de-scent or deodorize sportsmen while out in the field 200 by the use of ozone or hydroxyl and hydroperoxide ions.

Yet another object of the invention is to provide a method of deodorizing clothing with ozone so that it will not cause irritation or harm.

It is a further object of the invention to provide ozone in a compressed or generated form in a hand held container for application in the field by sportsmen.

Other objects and advantages of this invention will become apparent from the description of the preferred embodiments and the claims.

According to the present invention there is provided a method for the de-scenting of clothing used by sportsmen by the use of an oxidizing gas, namely, ozone or by ionization with UV light to produce hydroxyl and hydroperoxide ions. More particularly, the clothing of hunters can be treated with ozone or the hydroxyl and hydroperoxide ions either at home or in the field by the application of a small amount of ozone or the hydroxyl and hydroperoxide ions in order to remove the human scent or any other foreign scent. Also, the clothing of fishermen can be treated with the oxidizing gas while in the field to remove the odor of fish.

According to one embodiment of the invention, the human scent can be eliminated from clothing by applying a low volume stream of an oxidizing gas comprising ozone or hydroxyl and hydroperoxide ions directly on the hunter while he is wearing a hunting outfit. The gaseous stream is applied by an ozone generator 100 which is hand held or a catalytic ionizer containing UV light and easily transported by the hunter 200. The gaseous stream can be applied directly to the clothing being worn by the hunter in an open atmosphere 200 so as to be quickly diluted after it is passed over the clothing. Moreover, the gun or rifle or any other equipment, i.e. ammunition, arrows, scope, finders etc., of the hunter or sportsmen can be similarly treated 300 to remove the gun or rifle or equipment odor.

In accordance with another embodiment of the invention, the clothing of the hunter can be treated before or after the hunt by placing the clothing in a container i.e. a sack, bag or box while passing the oxidizing gas into the container in order to remove any human or other scent foreign to that environment.

Another embodiment of the invention is that the instrument can be carried with the hunter or hung upwind of the body so it descents the human scent traveling downwind.

Also, some certain clothing is not cleaned after every use by the hunter or sportsmen such as gloves, hats, jackets, boots, and need to be deodorized and decontaminated before next use.

According to a further embodiment of the invention, the odor of fish can be eliminated from a fisherman's clothing, body or equipment by the direct application of a stream of ozone gas or hydroxyl and hydroperoxide ions to the site of the fish odor. Additionally, a fisherman's hands can be deodorized with ozone so as to remove the fish odor without causing irritation.

Each of the methods can be practiced in the open in the field of sports activity utilizing a low volume gas generator. The clothing is not decolorized as in applications involved in high volumes of ozone as found in the garment industry where ozone is used to both de-size and/or decolorize denim garments. The oxidizing gas may be used alone or diluted with air as when packaged in a compressed gas form. Ozone which is produced by generators in amounts up to 8000 mg/hr can be compressed or diluted with an inert gas and compressed into small containers.

It is understood that the term "sportsmen" is meant to include those individuals who may hunt with a camera or who merely enter an environment to observe animals in their habitat.

Additionally, the term "fishermen" includes those individuals who handle the fish caught by others.

Hydroxyl and hydroperoxide are produced in a process known as "Radiant Catalytic Ionization" which utilizes ultra violet light which activates a photocatalytic target.

Small ozone generators such as those producing 1 to 25 lbs. of ozone per day can be utilized. Also the ozone can be applied from compressed ozone-filled containers similar to compressed air.

Low volume ozone generators which generate up to 65 mg/hr of ozone and are portable as well as high volume ozone generators are currently sold by EcoQuest International of Greenville, Tenn. which also sells the generators of hydroxyl and hydroperoxide ions.

It will be appreciated by persons skilled in the art that numerous variations and/or modifications may be made to the invention without departing from the spirit or scope of the invention as broadly claimed.

What is claimed is:

1. A method of eliminating scent, comprising:
transporting a portable ozone generator to a field for discharging a stream of ozone;
positioning the portable ozone generator in the field for use by a hunter, the hunter and game animals being present together in the field;
applying the stream of ozone onto the hunter and equipment used by the hunter in the field to eliminate human scent and other scent foreign to the field such that air deodorized with respect to the human scent and the other scent foreign to the field travels downwind of the hunter.

2. The method of claim 1 wherein the ozone is diluted with air and packaged in a compressed gas form.

3. The method of claim 1 wherein the portable ozone generator produces 1 to 25 lbs. of ozone per day.

4. The method device of claim 1 wherein the portable ozone generator produces up to 65 mg/hr of ozone.

5. The method of claim 1 wherein the portable ozone generator is positioned at least in part upwind of the hunter.

6. The method of claim 1 wherein the portable ozone generator is configured for hanging in the field.

7. The method of claim 1 wherein the portable ozone generator is configured for mounting on the hunter.

8. The method of claim 1 wherein the portable ozone generator is configured to apply the stream of ozone directly onto the hunter and to apply the stream of ozone to clothing being worn by the hunter.

9. The method of claim 1 wherein the portable ozone generator is configured to apply the stream of ozone directly onto the hunter and apply the stream of ozone to the equipment of the hunter.

10. A method to eliminate scent from hunters and hunting equipment while hunting in a field, comprising:
deploying a gaseous stream of ozone into an open atmosphere from an ozone producing device;
carrying the ozone producing device into the field, the ozone producing device being carried by a hunter; and
positioning the ozone producing device in the field upwind of game animals, the hunter, clothes worn by the hunter, or equipment used by the hunter while hunting in the field to eliminate the scents foreign to the field.

11. The method of claim 10, wherein the ozone producing device is hand-held.

12. A method of eliminating scent from hunters and hunting equipment while hunting in a field, comprising:
transporting a portable ozone generator to the field, the portable ozone generator being configured to be used by a hunter in the field;
generating a gaseous stream of ozone with the portable ozone generator, the portable ozone generator being configured to discharge the gaseous stream of ozone into an open atmosphere in the field surrounding the hunter as the hunter pursues animals;
positioning the portable ozone generator upwind of the hunter's scent in the field; and
passing the gaseous stream of ozone directly over the hunter, clothes worn by the hunter, and equipment used by the hunter while hunting in the field to eliminate human scent and other scent from the hunter's equipment foreign to the field, wherein the equipment comprises one of a gun, rifle, ammunition, arrows, scope, camera, rangefinder, or clothes.

13. The method of claim 12 wherein the ozone is configured to be packaged in a compressed gas form.

14. The method of claim 12 wherein the portable ozone generator is a handheld device configured to produce a gaseous stream of 1 to 25 lbs. of ozone per day when activated.

15. The method of claim 12, wherein positioning the portable ozone generator includes hanging the portable ozone generator in the field.

16. The method of claim 12, wherein the portable ozone generator is configured to be carried by the hunter in the field.

\* \* \* \* \*